United States Patent [19]

Heath

[11] Patent Number: 4,653,503

[45] Date of Patent: Mar. 31, 1987

[54] PHYSIOLOGICAL ELECTRODES FOR USE WITH MAGNETIC CONNECTOR

[75] Inventor: Roger L. Heath, Prospect Heights, Ill.

[73] Assignee: R2 Corporation, Skokie, Ill.

[21] Appl. No.: 554,835

[22] Filed: Nov. 23, 1983

[51] Int. Cl.[4] ............................................. A61B 5/04
[52] U.S. Cl. .................................................. 128/640
[58] Field of Search ............... 128/639, 640, 641, 644, 128/303.13, 795, 796, 798, 802, 803

[56] References Cited

U.S. PATENT DOCUMENTS

| | | | |
|---|---|---|---|
| 3,752,151 | 8/1973 | Robichaud | 128/641 |
| 3,810,258 | 5/1974 | Mathhauser | 339/12 R |
| 3,845,757 | 11/1974 | Weyer | 128/641 |
| 3,862,633 | 1/1975 | Allison et al. | 128/641 |
| 4,067,321 | 1/1978 | Oda et al. | 128/640 |
| 4,067,342 | 1/1978 | Burton | 128/641 |
| 4,112,941 | 9/1978 | Larimore | 128/641 |
| 4,211,456 | 7/1980 | Sears | 339/12 R |
| 4,259,965 | 4/1981 | Fukuda et al. | 128/640 |
| 4,270,543 | 6/1981 | Tabuchi et al. | 128/641 |

OTHER PUBLICATIONS

Proceedings of the 1964 17th Annual Conference on Engineering in Medicine and Biology, vol. 6, Robert Plonsey editor, Cleveland, Ohio.

Primary Examiner—William E. Kamm
Attorney, Agent, or Firm—Haight & Hofeldt

[57] ABSTRACT

Physiological electrodes are provided for use with a magnetic connector to complete an electrical circuit between the body of a patient and an electrical instrument. These electrodes contain a ferromagnetic material to complete a magnetic circuit with a magnetic member on an associated lead wire. This ferromagnetic material is included in an electrically conductive electrode element that contains an electrically conductive material, such as a saline gel, and the ferromagnetic material is isolated from the electrically conductive medium to prevent corrosion. The electrodes are provided with an arrangement for securing the electrode element to the body of a patient, and a separating member is provided to prevent the electrically conductive electrode element from contacting the skin of the patient in certain applications. In some embodiments, an appropriate restraining structure is provided to minimize the possibility of accidental disconnect.

32 Claims, 11 Drawing Figures

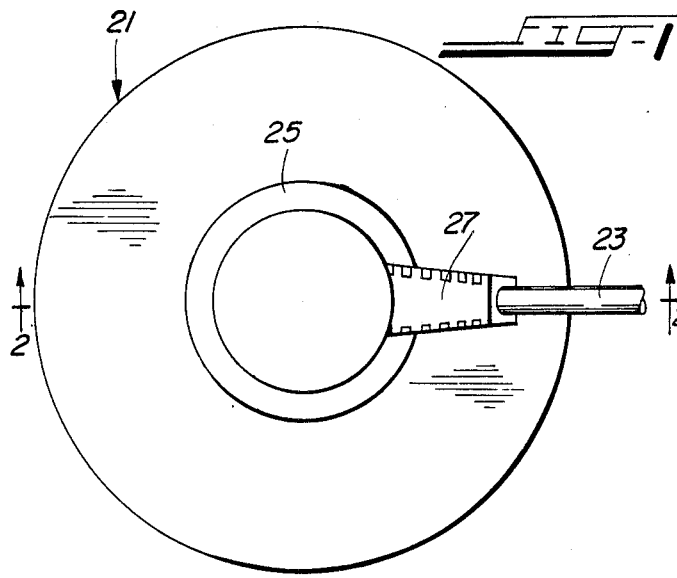
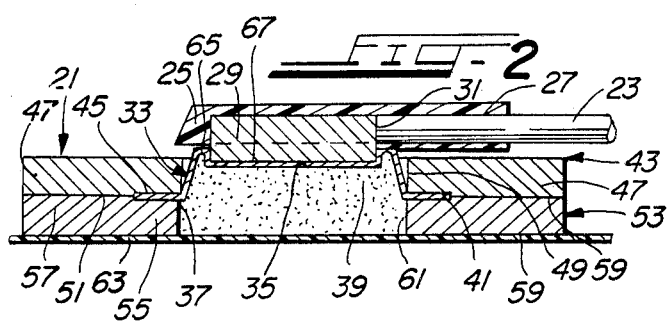
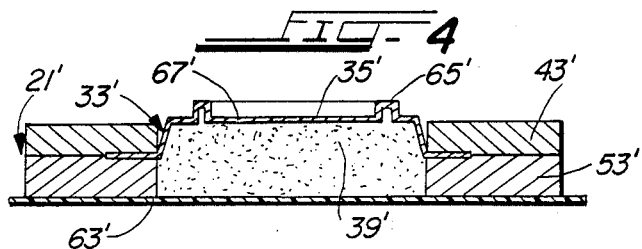
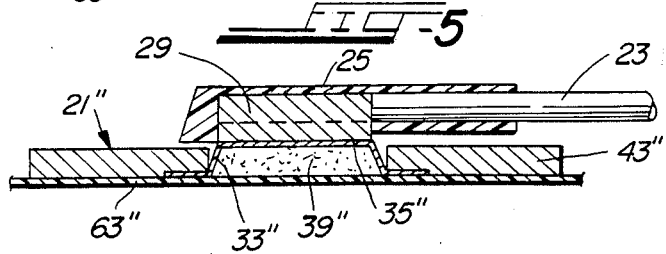
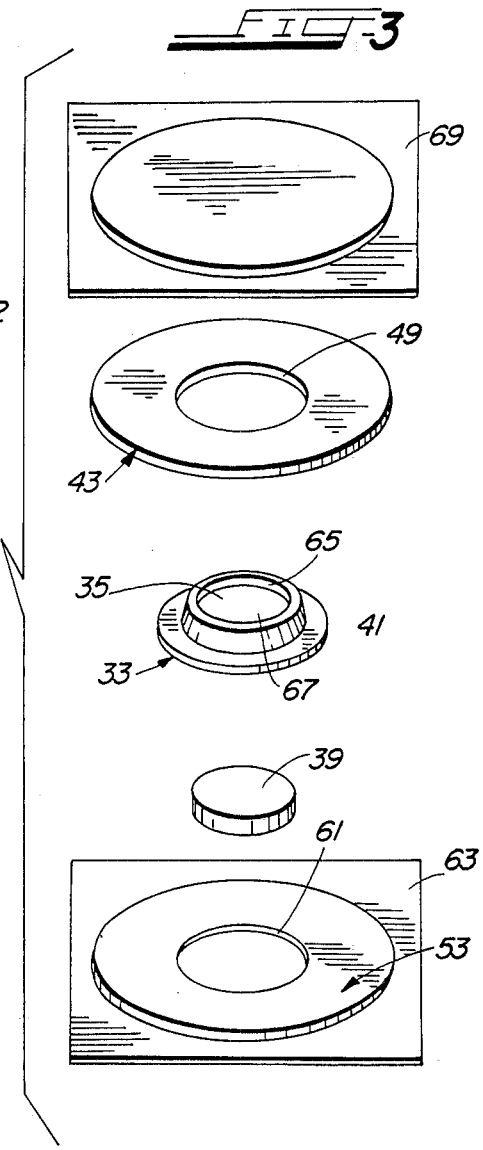
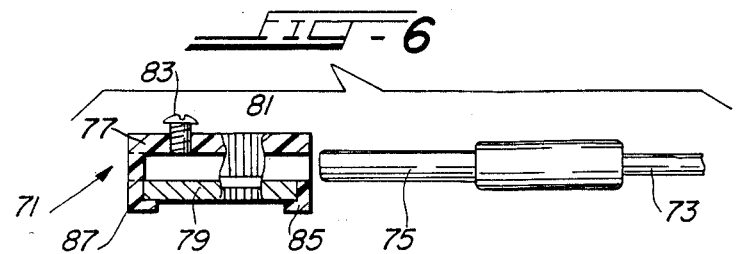

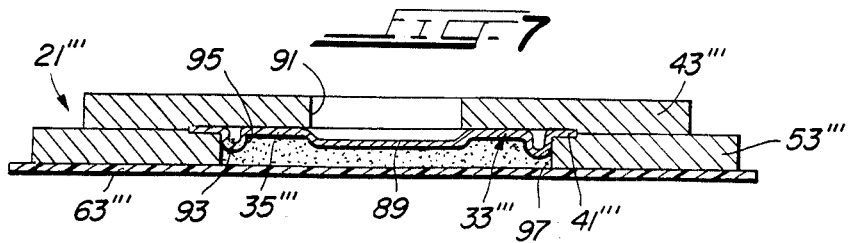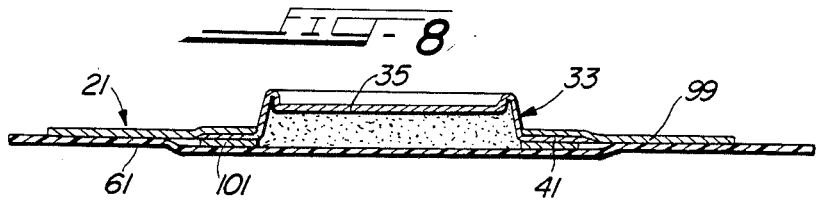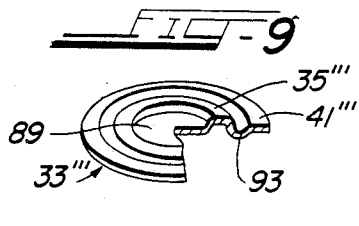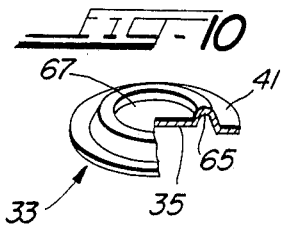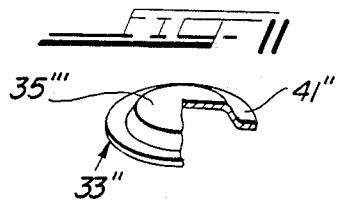

PHYSIOLOGICAL ELECTRODES FOR USE WITH MAGNETIC CONNECTOR

BACKGROUND OF THE INVENTION

1. Field of the Invention

This invention relates generally to physiological electrodes which may be selectively connected to an appropriate lead line by means of a magnetic connector, and more specifically, this invention relates to disposable pre-gelled physiological electrodes which may be selectively connected to a desired instrument by means of a magnetic connector.

2. Description of the Prior Art

A particular type of physiological electrode used primarily for monitoring physiological functions (such as heart monitoring by cardioscope, electrocardiogram or electrocardiograph) has been designated as "snap-type". This designation arises from the fact that these disposable electrodes are connected to an appropriate lead wire by means of a "snap connection, which includes an upstanding stem on the electrode and a mating member on the lead that "snaps" over the stem.

While these "snap-type" electrodes have desirable features and have been widely utilized in the medical field, they also have a number of significant drawbacks. One of the most significant problems is that the snap connection may be inadvertently broken so that the electrical continuity between the instrument and the patient is broken. This problem becomes greater with time as the snap loses its resiliency and the mechanical snap connection becomes weaker.

Another problem relates to the so-called "motion artifact" that occurs when snap electrodes are utilized. This "motion artifact" is a distortion or breaking up of the electrical signal received from the patient and is generally associated with movement of the conducting lead from the electrode to the instrument. It seems likely that this "motion artifact" is related to relative movement between the upstanding stem and the mating snap member. Loss of resiliency with age probably aggravates this problem also. The obvious disadvantage of such "motion artifact" is that the representation of the physiological function being monitored is distorted.

Still another disadvantage of the conventional snap-type electrode is delay or difficulty in making the snap connection initially. In an emergency situation, inserting the mating snap member over the stem can result in the loss of valuable seconds. This is particularly true when the electrode is placed over an area having a substantial amount of subcutaneous fat, so that as pressure is applied to make the snap connection, the yielding of the fleshy portion may make it difficult or even impossible to make the snap connection.

Magnetic structures to form an electrical connector have been suggested in the past, and the use of magnetic material in making the connection between an electrode and a lead wire has also been suggested. However, none of the prior art approaches has effectively dealt with problems such as the desirability of utilizing conventionally available magnets, as opposed to specially formed magnets; the necessity of protecting ferromagnetic material from corrosion; the reduction of motion artifact; the necessity of preventing metal contact with the skin in longer term applications; and other difficulties to be overcome in making a practical, effective and cost-justified disposable electrode to be used with a magnetic connector.

Accordingly, there is a significant need for a disposable electrode that can be quickly and easily connected to and disconnected from an associated lead wire, that will minimize accidental disconnection but which may still be easily disconnected when desired, and that reduces undesired motion artifact. When made for use with a magnetic connector, such a physiological electrode should be capable of being used with a conventionally available magnet, should provide protection from corrosion for the ferromagnetic material, particularly in the presence of a corrosive material such as a saline gel, positively prevent metal contact with the skin in prolonged electrode applications, and be cost-competitive with snap-type electrodes.

SUMMARY OF THE INVENTION

The physiological electrodes of the present invention are constructed to be utilized with a magnetic connector in such a fashion as to permit great ease of application, minimize accidental disconnection and greatly reduce motion artifact. These electrodes are also constructed to avoid the problems associated with a magnetic connector, while still capitalizing on the advantages such as those indicated above.

In describing the physiological electrode of this invention, the description will be that of a physiological monitoring electrode, although these electrodes are not so limited in application. Specifically, the description will be in terms of electrodes used in conjunction with instruments that monitor the operation of the heart, such as cardioscopes, electrocardiograms and electrocardiographs. (For ease of reference, the term "ECG" will be used to designate any or all of these devices.)

An ECG electrode constructed in accordance with the present invention includes an electrically conductive container or gel cup in which an electrically conductive medium such as a saline gel, may be contained. The electrically conductive medium provides an electrical connection between the skin of the patient and the electrically conductive container. At least a portion of the container provides the electrically conductive element of the physiological electrode.

The container is generally cup-shaped with either a generally frusto-conical or a generally cylindrical form. In each case, the cup-shaped container has an upwardly extending closed bottom portion and a downwardly extending open mouth portion. For ease of description, the electrode is assumed to be placed on top of the patient's body, although it could equally well be placed on the bottom or the side of the patient.

The upwardly extending closed bottom of the cup-shaped container has at least an area of ferromagnetic material. In the embodiments disclosed herein, the container is formed entirely of a ferrmagnetic material, but it is not necessary that the container be so formed.

In order to prevent corrosion of the ferromagnetic material, it is necessary to isolate it from corrosive forces, such as the salien gel that may be used as the electrically conductive medium. This is achieved by an appropriate protective coating, such as by plating the ferromagnetic container with a corrosion-resistant conductive metal, such as tin. In order to increase the efficacy of the electrode, it is also desirable to place a chloride of the corrosion-resistant metal, such as a stannous chloride, adjacent the tin. One way of achieving this is to utilize a conductive coating that includes the stannous chloride.

In order to make the magnetic connection to the electrode, a magnetic member such as a permanent magnet is electrically connected to the instrument lead wire. For some applications, it is desirable to provide a restraining arrangement to aid in minimizing the chance of an accidental disconnect. Such a restraining arrangement can take the form of a raised ridge that forms a cavity on the closed bottom of the container into which the magnetic member may be placed. In another approach, a depression may be formed in the closed end of the container to receive the magnetic member. In still other applications, such as for a so-called "rest EKG" where a quick connect and disconnect is more important than a secure connection, no restraining arrangement may be desired.

When an ECG electrode is applied to a patient, the electrically conductive electrode element should not be permitted to contact the skin. The primary reason for this desired separation of the electrically conductive electrode element from the skin is that if the patient is subjected to an electrosurgical operation the radio frequency energy could pass through the electrically conductive material, resulting in burns to the patient. Also, the radio frequency energy could be conveyed back to the monitoring instrument and thus create a risk of damage to the ECG monitor. The present invention separates the electrically conductive electrode element from the skin by means of a layer of non-conductive material, such as a conventional foam material.

The foam material that separates the electrode element from the skin of the patient may also be a part of the structure for securing the electrode element to the patient. Thus, an outwardly extending flange may be formed on the cup-shaped container as a part of the arrangement for securing the electrode element to the patient. A first layer of foam material may be formed with a central opening through which the cup-shaped container extends, with the bottom of a first or inner portion of the foam layer, formed in a generally annular ring, located on the top of the flange. An adhesive material may be placed on the bottom surface of the first foam ring so that the first portion thereof adheres to the top of the flange. A second layer or foam ring then provides the separating structure previously referred to. This second foam ring has a central opening substantially the same diameter as the mouth of the cup-shaped container, so that the conductive medium can contact the skin of the patient. The second foam ring may be provided with an adhesive material on both the top and bottom surfaces thereof. A first or inner portion of the top surface of the second ring then adheres to the bottom of the flange, while a second or outer portion may be adhered to a second or outer portion of the first foam ring. The bottom surface may then be adhered to a patient when desired. In order to maintain the conductive medium in place and prevent drying out, if a gel is utilized, a suitable cover may be adhered to the bottom surface of the second foam ring until it is desired to attach the electrode to a patient.

Another reason for separating the electrically conductive electrode elements from the skin of the patient is that over a period of time skin irritation may result. It is believed that this irritation results from a galvanic action occurring between the electrically conductive electrode element and the skin. However, in some cases the electrode may not be left on sufficiently long to worry about skin irritation and may be used in circumstances when there is no risk of an electrosurgical operation. Again, a prime example is the rest EKG electrode. In this case, the second foam ring may not be needed and the adhesive on the outer portion of the first foam ring may be utilized to adhere the electrode to the skin of the patient.

With the invention described, connection between the instrument lead wire and the electrode may be quickly and easily made by merely bringing the magnetic member adjacent the ferromagnetic material of the electrode. By the utilization of an appropriate conventional permanent magnet, sufficient magnet force may be generated to minimize accidental disconnections of the electrode from the instrument, which may be enhanced by use of a suitable restraining structure. It has been found that motion artifact is greaty descreased, presumably because even though the magnet may be rotated a continuous contact is still maintained between the surface of the magnet and the ferromagnetic material of the electrode. In this fashion, a practical and cost-efficient physiological electrode for use with a magnetic connector is provided.

These and other objects, advantages and features of this invention will hereinafter appear, and for purposes of illustration, but not of limitation, exemplary embodiments of the subject invention are shown in the appended drawing.

BRIEF DESCRIPTION OF THE DRAWING

FIG. 1 is a top plan view of a physiological electrode constructed in accordance with the present invention, shown connected to a lead wire by a magnetic connector.

FIG. 2 is a cross-sectional view taken along line 2—2 of FIG. 1.

FIG. 3 is an exploded view illustrating the parts of the physiological electrode of FIGS. 1 and 2.

FIG. 4 is a cross-sectional view, without the magnetic connector, of another embodiment of the physiological electrode of FIG. 2.

FIG. 5 is a cross-sectional view, with the magnetic connector, of another embodiment of the physiological electrode of FIG. 1.

FIG. 6 is a cross-sectional view of an adaptor to convert an instrument lead wire to a magnetic connector.

FIG. 7 is a cross-sectional view, without the magnetic connector, of another embodiment of the physiological electrode of FIG. 1.

FIG. 8 is a cross-sectional view, without the magnetic connector, of another embodiment of the physiological electrode of FIG. 1.

FIG. 9 is a perspective, partially broken away view of the electrode element container structure of FIG. 7.

FIG. 10 is a perspective, partially broken away view of the electrode element container structue of FIG. 2.

FIG. 11 is a perspective, partially broken away view of the electrode element container structure of FIG. 5.

DETAILED DESCRIPTION OF THE PREFERRED EMBODIMENTS

A preferred embodiment of a disposable physiological electrode 21 for use with a magnetic connector is illustrated in FIGS. 1-3.

An electrical lead 23 is connected to a suitable instrument (not shown) to convey electrical signals between electrode 21 and the instrument. For purposes of this description, the instrument will be considered to be an ECG monitor. Electrical lead 23 extends into a formed plastic end piece 25 through an extended portion 27. As may be best seen in FIG. 2, a magnetic member 29, such as a permanent magnet, is secured in the end piece 25. Extending portion 27 is also formed of a relatively rigid material, to provide a lifting member to assist in disengaging the magnetic member 29, when desired to do so. A good electrical bond is formed between lead wire 23 and magnetic member 29 at area 31, such as by sealing wire 23 and magnetic member 29 in place and locating a conductive paint at the joint.

While the magnetic member 29 may be mounted in any suitable fashion at the end of lead wire 23, in this preferred embodiment the magnetic member 29 is a conventional cylindrical magnet secured by a force fit in the molded end piece 25. Additional bonding could be provided by use of an appropriate adhesive, if desired.

Electrode 21 includes an electrode element 33, the form of which may be better visualized from the partly broken away perspective view of FIG. 10. In this preferred embodiment, the electrode element 33 is in the form of a cup-shaped container. The cup-shaped container is generally frusto-conical in form with a closed bottom 35 at the narrower diameter end and an open mouth 37 at the larger diameter end. An electrically conductive medium 39, such as a saline gel, is located in the cup-shaped container of electrode element 33.

At least the closed bottom 35 of electrode element 33 must be formed of an electrically conductive material in order to transmit electrical signals passing between the skin of the patient and the magnetic member 29 through the conductive medium 39. In addition, at least an area of ferromagnetic material must be located at the closed end 35 of electrode element 33 in order to provide a complete magnetic circuit for the magnetic member 29 to permit the making of the magnetic connection between line 23 and electrode 21.

Although other approaches could be utilized, such as making the element 33 out of conductive plastic with an area of ferromagnetic material at end 35, in this preferred embodiment the entire electrode element 33 is formed of an electrically conductive ferromagnetic material, such as a suitable steel. However, such a ferromagnetic material is subject to corrosion, especially if the electrode element 33 is utilized as a gel cup and the electricaly conductive medium is a corrosive material, such as a saline gel. Accordingly, in order to protect the ferromagnetic material, a layer of tin or other corrosion-resistant electrically conductive material may be plated or coated over the interior of electrode element 33. In practice, it would generally be more efficient to plate the entire electrode element 33. By then utilizing a chloride of the plated material, such as stannous chloride for the tin, the advantages of a tin-stannous chloride electrode, as explained in Applicant's co-pending patent application entitled "Tin-Stannous Chloride Electrode Element", Ser. No. 06/476,332, filed on Mar. 17, 1983 now abandoned. The stannous chloride may be placed adjacent the tin by incorporatinig it into an electrically conductive coating that is coated over at least a portion of the interior of electrode element 33.

In order to attach electrode element 33 to the skin of a patient, electrode 21 must include some type of securing arrangement. This securing arrangement can include an outwardly extending flange 41 that is affixed to the electrode element 33. In this preferred embodiment, flange 41 is generally annular in shape and is located adjacent the mouth 37 of electrode element container 33. Although flange 41 may be affixed to electrode element 33 in any appropriate fashion, in this preferred embodiment it is integrally formed with the frusto-conical body of element 33.

The securing arrangement also may include a layer of electrically non-conductive material 43, such as a conventional plastic foam. In this preferred embodiment, layer 43 is a generally annular ring having a first or inner portion 45 that is substantially coextensive with flange 41, and a second or outer portion 47. A central opening 49 is generally circular in shape with a diameter substantially the same as the diameter of electrode element 33 at the top of flange 41. A suitable adhesive 51 is located on the bottom of foam ring 43 to attach ring 43 to flange 41 at portion 45. The adhesive 51 on the bottom surface of portion 47 of foam ring 43 may be utilized to attach the electrode element 33 to a patient.

When an ECG electrode is to be utilized on a patient upon whom an electrosurgical operation may be performed, or if the electrode is to be left on the body for a significant period of time, it is desirable to separate the electrically conductive electrode element from the skin of the patient. Therefore, in this preferred embodiment a second layer of non-conductive material 53, such as a generally annular ring of plastic foam, is utilized. Foam ring 53 has a first or inner portion 55 generally coextensive with flange 41 and a second or outer portion 57. A suitable adhesive material 59 may be located on both the top and bottom surfaces of foam ring 53. Adhesive 59 on the top surface of portion 55 of ring 53 adheres to the bottom of flange 41, while the adhesive material 59 on the top surface of portion 57 of foam ring 53 adheres to the bottom surface of portion 47 of foam ring 43. In this fashion, foam ring 53 serves both to separate electrode element 33 from the skin of the patient and is also an integral portion of the structure utilized to secure electrode element 33 to the patient.

A central opening 61 is formed in the foam ring 53. Opening 61 is generally circular in shape and has a diameter substantially the same as the diameter of the mouth of electrode element 33. To simplify manufacturing procedures, the diameter of opening 61 may be the same as the diameter of opening 49 in foam ring 43, so that foam rings 43 and 53 are substantially interchangeable prior to assembly. Opening 61 permits the electrically conductive material 39 to contact the skin of the patient and form an electrically conductive path from the skin of the patient to the electrode element 33. In order to maintain the electrically conductive material in the electrode element 33 and to prevent the material 39 from drying out, a cap or cover 63 may be releasably attached to the adhesive material 59 on the bottom surface of foam ring 53. This cover 63 is a thin plastic material that may be stripped from the electrode 21 to permit the adhesive 59 on foam ring 53 to attach the electrode to the skin of a patient.

In order to make the attachment between the magnetic member 29 and the closed bottom 35 of electrode element 33 more secure, a suitable restraining structure 65 may be utilized. In the preferred embodiment of FIGS. 1–3, the restraining structure 65 is an upwardly extending ridge that forms a cavity 67 into which the magnetic member 29 may be inserted. Ridge 65 may be affixed to electrode element 33 in any appropriate fashion, but in this preferred embodiment ridge 65 is integrally formed with electrode element 33 about the outer periphery of the closed end 35 of element 33. It may also be noted that in this preferred embodiment the closed end 35 of electrode element 33 extends above the top surface of foam ring 43.

In the exploded view of FIG. 3, a strip of plastic foam material 69 is shown to illustrate how the rings 43 and 53 may be stamped from this material. This exploded view is also helpful in visualizing how the flange 41 rests on the top surface of foam ring 53, with the electrically conductive material 39 located in the electrode element 33 and foam ring 43 resting on the top of flange 41 and the outer portion of ring 53.

Another embodiment of the electrode 21 of this invention is illustrated in FIG. 4. In this embodiment, a larger electrode area is utilized. With similar elements identified by prime numerals corresponding to the numerals utilized in describing the embodiment of FIGS. 1–3, it may be seen that the extending ridge 65' is spaced inwardly from the outer periphery of the closed end 35' of the electrode element 33', so that the cavity 67' still snugly accepts the same magnetic member 29, even though the electrode area is increased. In all other respects, this embodiment is substantially the same as the embodiment of FIGS. 1–3.

In some applications, the electrodes will only be attached to the patient for a short period of time. A prime example is the so-called "rest EKG" electrodes. In the rest EKG situation, a tracing of heart action is obtained by using a multiplicity of electrodes at various locations, usually a minimum of 7 and going to as high as 15 or more. These electrodes are only on the body for the short period of time required to make the test, usually no more than 5 or 10 minutes. Also, the rest EKG electrodes are not utilized in conjunction with an electrosurgical operation.

For the rest EKG electrodes, there is no need to separate the electrically conductive electrode element from the body, as there is no concern for radio frequency energy burns or the establishment of an electrolytic or galvanic action. The main attributes of the rest EKG electrode are that it must be easily and quickly connectible to the EKG monitor and it must have a low per-unit cost.

With reference to the embodiment of FIG. 5, similar parts of the electrode 21" have been identified by the same numerals with a double prime notation. Thus, it may be seen that the second foam ring 53 has been deleted, since it is not necessary to separate the electrode element 33" from the skin of the patient. This leaves only the foam ring 43" for attaching the electrode element 33" to the patient. Also, the closed bottom 35" of the cup-shared electrode element 33" does not include the projecting ridge 65 to restrain the magnetic member 29. The reason for this omission is that in the case of the rest EKG electrodes it is more important to be able to quickly connect and disconnect the magnet to the electrode than to provide the additional restraint against accidental disconnection that is needed for ECG electrodes that are going to be on the patient's body for a much longer period of time.

In the embodiment of FIG. 5, the same magnetic element 29 on the end of lead wire 23 is utilized as in the embodiment of FIG. 2. However, in some cases it is necessary to be able to modify existing leads for use with the rest EKG of FIG. 5, rather than utilizing the special end piece 25 encasing the magnetic member 29. Accordingly, an adapter 71 to make such a conversion is illustrated in FIG. 6. As shown in FIG. 6, a lead wire 73 normally has some type of projecting prong 75. The adapter 71 is capable of adapting any size of or shape of prong 75 for use as a magnetic connector.

Adaptor 71 has a molded plastic body 77 in which a magnetic member 79 is mounted. A threaded opening 81 is provided in one side of the molded housing 77 to receive a threaded set screw to secure prong 75 in the adaptor 71.

A pair of projecting shoulders 85 and 87 define the amount of magnet 79 that is available for contact. The distance between shoulders 85 and 87 is chosen to be substantially the same width as the diameter of closed end 35" of electrode element 33". Thus, the adaptor 71 fits over the closed end 35" of electrode element 33" with a relatively tight fit. Since the connection to rest EKG electrodes 21" does not need to be as secure a connection as in the ECG electrodes having a much longer time of application, the magnet 79 does not have to produce as strong a magnetic field as does the magnet 29. This permits the use of a less expensive magnet, thus reducing the cost of the adaptor 71.

Still another embodiment of a physiological electrode 21''' is illustrated in FIG. 7. In this case, the electrode element 33''' has a depressed portion 89 formed in the closed bottom 35''' of the electrode element 33'''. Depression 89 is adapted to receive the magnet 29 through an opening 91 formed in the first foam ring 43'''. The diameter of opening 91 is substantially the same as the diameter of magnetic member 29.

An extending protection, in the form of a generally annular ring, extends downwardly from the closed bottom 35''' of electrode element 33''' to form the cup-shaped container 95. In this case, the interior of cup-shaped container 95 is shallower and more cylindrical in shape than is the interior of electrode element 33 in the embodiment of FIG. 2. A flange 41''' extends outwardly from the projection 93. Although projection 93 and flange 41''' could be separately formed and affixed to the electrode element 33''', in this preferred embodiment these elements are formed as an intergral portion of the electrode element. An opening 97 formed in the second foam ring 53''' has a diameter substantially the same as the diameter of the container formed by the projections 93. A better visualization of the structure of electrode element 33''' is achievable by reference to the partially broken away perspective view of FIG. 9.

A further embodiment of the electrode 21 is illustrated in FIG. 8. This embodiment utilizes the same electrode element 33 as the embodiment of FIG. 2, but instead of the foam ring 43, a cloth ring 99 provides the top non-conductive layer. Also, a second non-conductive layer 101 is much smaller than the foam ring 53 and may be made of any suitable non-conductive material, such as a relatively thin plastic material. Some users feel that the cloth adheres to the skin better and that it is more comfortable for the patient. Choice between the embodiments of FIGS. 2 and 8 is primarily a matter of personal preference.

It should be understood that although certain alternative and modified approaches or embodiments have been disclosed herein, these and various other modifications, changes and variations may be made in the arrangement, operation and details of construction of the elements disclosed herein without departing from the spirit and scope of this invention.

I claim:
1. A physiological electrode for use with a magnetic connector comprising:

an electrically conductive gel, an electrically conductive electrode element formed as a container for said conductive gel, said container having an open mouth at one end, the other end of said container being closed and having at least an area of ferromagnetic material to be engaged by the magnetic connector, at least some of said electrically conductive gel being located in said container;

isolating means to prevent said conductive gel from contacting the ferromagnetic material of said electrode element; and securing means to attach said electrode element to a patient with the gel contacting the skin of the patient.

2. A physiological electrode as claimed in claim 1 and further comprising separating means to positively preclude said electrode element from contacting the skin of the patient.

3. A physiological electrode as claimed in claim 1 wherein said electrode element is formed completely of ferromagnetic material.

4. A physiological electrode as claimed in claim 3 wherein said isolating means comprises a layer of a corrosion-resistant conductive metal plated over the ferromagnetic material of said electrode element.

5. A physiological electrode as claimed in claim 4 wherein said isolating means further comprises a conductive coating including a chloride of said corrosion-resistant metal.

6. A physiological electrode as claimed in claim 5 wherein said corrosion-resistant metal is tin and said chloride is stannous chloride.

7. A physiological electrode as claimed in claim 1 wherein said securing means comprises:
   an outwardly extending flange affixed to said electrode element;
   a layer of electrically non-conductive material having an inner portion generally coextensive with said flange and an outer portion; and
   an adhesive material on the bottom surface of said non-conductive layer adhering to the top of said flange at said inner portion and to adhere to the skin of the patient at said outer portion when the electrode is attached to the patient.

8. A physiological electrode as claimed in claim 7 wherein the closed end of said electrode element container extends above said non-conductive layer.

9. A physiological electrode as claimed in claim 7 wherein the closed end of said electrode element has a depressed portion into which the magnetic connector may be inserted.

10. A physiological electrode as claimed in claim 7 wherein said securing means further comprises:
    a second layer of electrically non-conductive material to separate said electrode element from the skin of the patient to preclude any portion of said electrode element from contacting the skin of the patient;
    adhesive material on the top surface of said second non-conductive layer adhering to the bottom of said flange; and
    adhesive material on the bottom surface of second non-conductive layer to adhere to the skin of the patient when the electrode is attached to the patient.

11. A physiological electrode as claimed in claim 10 wherein:

said second non-conductive layer has an inner portion generally coextensive with said flange and an outer portion; and said adhesive material on the top surface of said second non-conductive layer adheres to the bottom of said flange at said inner portion and to said outer portion of said first non-conductive layer at said outer portion.

12. A physiological electrode as claimed in claim 1 and further comprising restraining means to aid in preventing undesired disconnection of the magnetic connector from said area of ferromagnetic material.

13. A physiological electrode as claimed in claim 12 wherein said restraining means comprises an upwardly extending ridge on the closed end of said electrode element container to retard lateral movement of the magnetic connnector.

14. A physiological electrode as claimed in claim 1 and further comprising a cover over said securing means to be removed when the electrode is to be attached to a patient.

15. A physiological electrode for use with a magnetic connector comprising:
    an electrically conductive inverted cup-shaped electrode element having an open mouth at one end and an upwardly extending bottom at the other end, at least a portion of the upwardly extending bottom of said cup-shaped electrode element including ferromagnetic material;
    an electrically conductive medium located in said cup-shaped electrode element;
    a generally annular flange affixed to and exending outwardly from said cup-shaped electrode element adjacent the open mouth thereof;
    a generally annular ring of electrically non-conductive material having a central opening with a diameter substantially the same as the diameter of said electrode element at the top of said flange, a first portion of said annular ring being substantially coextensive with said flange and a second portion extending beyond said flange; and
    an adhesive on the bottom surface of said annular ring so that said first portion thereof adheres to the top surface of said flange and the second portion may be adhered to the skin of a patient to attach the electrode to the patient.

16. A physiological electrode as claimed in claim 15 and further comprising:
    a second generally annular ring of electrically non-conductive material having a central opening with a diameter substantially the same as the diameter of the open mouth of said cup-shaped electrode element, said second annular ring positioned to be between said electrode element and the patient to prevent any portion of said electrode element from contacting the skin of the patient;
    an adhesive material on the top surface of said second annular ring, an inner portion of said second annular ring being generally coextensive with said flange and said adhesive material on said inner portion adhering to the bottom of said flange, and an outer portion of said second annular ring with said adhesive material on said outer portion adhering to said second portion of said first annular ring; and
    an adhesive material on the bottom surface of said second annular ring to adhere to the skin of the patient when the electrode is attached to the patient.

17. A physiological electrode as claimed in either claim 15 or claim 16 and further comprising a cover releasable adhered to by the adhesive material that is to attach the electrode to the patient, said cover holding said conductive medium in said cup-shaped electrode with a substantially air-tight seal until the electrode is attached to the patient.

18. A physiological electrode as claimed in claim 15 wherein:
said cup-shaped electrode element is constructed of a ferromagnetic material;
a layer of tin is plated over said ferromagnetic material; and
stannous chloride is located between said tin-plated electrode element and said conductive medium.

19. A physiological electrode as claimed in claim 15 wherein:
said cup-shaped electrode element has a frusto-conical form with the closed bottom of said electrode element being at the smaller diameter end and the open mouth of said electrode element being at the larger diameter end; and
the bottom of said electrode element extends above said annular ring.

20. A physiological electrode as claimed in claim 19 wherein the electrode further comprises an upstanding ridge formed on the bottom of said electrode element to form a cavity into which the magnetic connector may be placed.

21. A physiological electrode as claimed in claim 20 wherein said flange is integrally formed with said electrode element adjacent the open mouth thereof.

22. A physiological electrode for use with a magnetic connector comprising:
an electrically conductive medium;
an electrically conductive electrode element formed as a container for said conductive medium, said container having an open mouth at one end, the other end of said container being closed and having at least an area of ferromagnetic material, at least some of said electrically conductive medium being located in said container;
securing means to attach said electrode element to a patient with the conductive medium contacting the skin of the patient; and
separating means to be positively preclude said electrode element from contacting the skin of the patient to whom the electrode is attached.

23. A physiological electrode as claimed in claim 22 wherein said separating means is a part of said securing means, and said securing means comprises:
a first layer of electrically non-conductive material having a first portion and a second portion;
an adhesive material on the bottom surface of said first non-conductive layer, said adhesive material on said first portion adhering to said electrode element and said adhesive material on said second portion to adhere to a second layer of electrically non-conductive material;
an opening formed in said first non-conductive layer for making the magnetic connection to said electrode element;
said second layer of electrically non-conductive material having a first portion and a second portion, said second non-conductive layer providing said separating means;

an adhesive material on the top surface of said second non-conductive layer, said adhesive material on said first portion adhering to said electrode element and said adhesive material on said second portion adhering to said second portion of said first non-conductive layer;
an adhesive material on the bottom surface of said second non-conductive layer to adhere to the skin of the patient; and
an opening formed in said second non-conductive layer to permit said conductive medium contact the skin of the patient.

24. A physiological electrode as claimed in claim 23 wherein the closed end of said electrode element has a depression formed therein to receive the magnetic connector.

25. A physiological electrode as claimed in claim 23 wherein the closed end of said electrode element extends upwardly from said first layer of non-conductive material through said opening therein and a raised ridge is formed on the closed end of said electrode element to form a cavity to receive the magnetic connector.

26. A physiological electrode for use with a magnetic connector having a magnetic member comprising:
an electrically conductive medium;
an electrically conductive inverted cup-shaped member to contain said conductive medium, at least a portion of the upwardly extending bottom of said cup-shaped member including ferromagnetic material, at least some of said electrically conductive medium being located in said cup-shaped member;
restraining means to aid in maintaining the magnetic member on the separately extending bottom of said cup-shaped member adjacent the ferromagnetic material;
a flange extending outwardly from said cup-shaped member;
securing means to attach the electrode to a patient;
engaging means to fasten said flange to said securing means; and
separating means to positively preclude any portion of said cup-shaped member from contacting the skin of the patient.

27. A physiological electrode as claimed in claim 26 wherein said restraining means comprises a depression formed in the upwardly extending bottom of said cup-shaped member to receive the magnetic member.

28. A physiological electrode as claimed in claim 26 wherein said restraining means comprises a raised ridge located on the upwardly extending bottom of said cup-shaped member to define a cavity into which the magnetic member may be placed.

29. A disposable physiological electrode for use with a magnetic connector having a magnetic member comprising:
an electrically conductive medium;
an electrically conductive electrode element;
an annular projection affixed to and extending downwardly from said electrode element to form a container for said electrically conductive medium;
a generally annular flange affixed to said electrode element and extending outwardly from said annular projection;
a depression formed in said electrode element to receive the magnetic member, said depression extending downwardly into the container formed by said annular projection;

at least an area of ferromagnetic material in said depression;

a first layer of electrically non-conductive material having a central opening substantially the size of said depression, a first portion of said first non-conductive layer extending from said opening to the outer edge of said flange and a second portion;

an adhesive material on the bottom surface of said first non-conductive layer to adhere to the top of said flange at said first portion thereof;

a second layer of electrically non-conductive material having a central opening with a diameter substantially the same as the diameter of the container formed by said annular projection; and an adhesive material on the top surface of said second non-conductive layer to adhere to the bottom of said flange.

30. A disposable physiological electrode for use with a magnetic connector including a magnetic member comprising:

an electrically conductive medium;

an inverted cup-shaped member formed of a ferromagnetic material to contain said conductive medium, the upwardly extending bottom of said cup-shaped member adapted to be engaged by the magnetic member, at least some of said conductive medium being located in said cup-shaped member;

isolating means to prevent said conductive medium from contacting the ferromagnetic material of said cup-shaped member;

an annular flange affixed to said cup-shaped member and extending outwardly adjacent the open mouth of said cup-shaped member;

a first annular ring of electrically non-conductive material having a diameter greater than the diameter of said annular flange and formed with a central opening having a diameter slightly larger than the diameter of said cup-shaped member at said flange;

an adhesive material affixed to the bottom surface of said first annular ring, the body of said cup-shaped member extending upwardly through the central opening of said first annular ring with the adhesive on the bottom surface of said first annular ring adhering to the top of said flange;

a second annular ring of electrically non-conductive material having a diameter greater than the diameter of said annular flange and formed with a central opening approximately the size of the mouth of said cup-shaped member; and an adhesive material affixed to at least the top surface of said second annular ring with the bottom of said flange being positioned on the top surface of said second annular ring so that said cup-shaped member is positively separated from the skin of the patient.

31. A disposable physiological electrode as claimed in claim 30 wherein said isolating means comprises:

a layer of tin plated over said ferromagnetic material; and a conductive coating including stannous chloride coated over said tin.

32. A physiological electrode for use with a magnetic connector comprising:

an electically conductive medium;

an electrically conductive electrode element formed as a container for said conductive medium said container having an open mouth at one end, the other end of said container being closed and having at least an area of ferromagnetic material to be engaed by the magnetic connector, at least some of said electrically conductive medium being located in said container;

isolating means to prevent said conductive medium from contacting the ferromagnetic material of said electrode element; and securing means to attach said electrode element to a patient with said conductive medium contacting the skin of the patient.

* * * * *